United States Patent [19]
Buysch et al.

[11] Patent Number: 5,965,472
[45] Date of Patent: Oct. 12, 1999

[54] RECOVERY OF CATALYST SYSTEMS FROM DIARYL CARBONATE-CONTAINING REACTION SOLUTIONS BY SUSPENSION CRYSTALLIZATION

[75] Inventors: Hans-Josef Buysch; Carsten Hesse, both of Krefeld; Johann Rechner, Kempen; Hans-Peter Wirges, Krefeld, all of Germany

[73] Assignee: Bayer AG, Germany

[21] Appl. No.: 08/829,929

[22] Filed: Apr. 1, 1997

[30] Foreign Application Priority Data

Apr. 9, 1996 [DE] Germany .............................. 196 13 991

[51] Int. Cl.$^6$ .............................. B01J 38/52; B01J 38/50; B01J 20/34; C07C 69/96
[52] U.S. Cl. ................................ 502/33; 502/20; 502/24; 502/29; 558/270; 558/274
[58] Field of Search .................................. 502/20, 24, 29, 502/33; 558/270, 274

[56] References Cited

U.S. PATENT DOCUMENTS

| | | | |
|---|---|---|---|
| 5,239,106 | 8/1993 | Shafer | 558/274 |
| 5,312,955 | 5/1994 | Pressman et al. | 558/260 |
| 5,495,038 | 2/1996 | Buysch et al. | 558/274 |

FOREIGN PATENT DOCUMENTS 0 687 666   12/1995   European Pat. Off. .

OTHER PUBLICATIONS

Orbit Abstract of EP 0 687 666 (Dec. 20, 1995).
Ullman's Encyclopedia of Industrial Chemistry, vol. B–2, Unit Operations I, Chapter 25: Stirring, pp. 25–1 through 25–6 (1988). no month.
Chem.–Ing.–Tech.57, Nr. 2, pp. 91–95 (1985). no month.

*Primary Examiner*—Michael Lewis
*Assistant Examiner*—Alexander G. Ghyka
*Attorney, Agent, or Firm*—Connolly & Hutz

[57] ABSTRACT

Catalyst systems with a content of a platinum-group-metal catalyst, a co-catalyst, a quaternary salt and a base for the oxidative carbonylation of aromatic hydroxy compounds to the corresponding diaryl carbonates are according to the invention obtained as a mother liquor by suspension crystallization and can be returned into the carbonylation reaction or worked up to valuable materials. The crystallizate, which consists predominantly of diaryl carbonate and the parent aromatic hydroxy compound, is worked up to pure diaryl carbonate and pure hydroxy compound.

7 Claims, No Drawings

RECOVERY OF CATALYST SYSTEMS FROM DIARYL CARBONATE-CONTAINING REACTION SOLUTIONS BY SUSPENSION CRYSTALLIZATION

The present invention relates to a method for recovering catalyst systems from diaryl carbonate-containing reaction solutions by suspension crystallization, wherein a -crystallizate and a mother liquor containing the catalyst system are obtained. The mother liquor can be returned into the reactor for producing the diaryl carbonate or worked up to valuable materials. The crystallizate is worked up to pure diaryl carbonate and pure hydroxy compound.

U.S. Pat. No. 5,239,106 teaches the separation of diphenyl carbonate from catalyst-containing reaction solutions by crystallizing the 1:1 adduct with phenol, consisting of 30.5 wt % phenol and 69.5 wt % diphenyl carbonate, from reaction mixtures with the aid of suspension crystallization. Disadvantageous with this method is the restriction to a narrow concentration range to enable the 1:1 adduct to be isolated with sufficiently high yield, i.e. diphenyl carbonate concentrations of at least 50 wt % to 70 wt %. In order that the resulting suspensions may still be processable with the aid of filters, at least a two-stage method involving sophisticated equipment is required. Moreover the catalyst system cannot be separated completely by this method, since the filtered-off crystals still possess adhering mother liquor and inclusions of mother liquor. During the subsequent working up of the 1:1 adduct by distillation, these non-separated catalyst components have a negative effect through the catalysis of by-product formation and DPC decomposition. The proposed washing of the crystallizate with a mixture of 9% water and 91% phenol reduces the yield by dissolving large parts of the 1:1 adduct. Moreover this treatment increases the water content of the adduct crystals, which causes DPC losses due to hydrolysis in the subsequent distillation columns, i.e. in those for the DPC isolation and for the separation of water from the washing solution used. Moreover important process parameters are not disclosed in U.S. Pat. No. 5,239,106, e.g. on the nature of the reactor, on the temperature control, agitator geometry, agitation rate etc.

To permit reaction solutions with a DPC content of less than 50 wt % also to be processed by this method, an enrichment by distillation, with the disadvantages described above of a distillation in the presence of catalyst components, is imperative. In addition a thermal stress of the reaction solution leads to a deactivation of the catalyst system, which requires an expensive fresh feeding of the catalyst components into the process. All these disadvantages described make the method inflexible and unattractive and prevent a technical realization.

EP-A 687 666 describes a method for the purification of diphenyl carbonate by the fractional melt crystallization of highly concentrated reaction solutions in the temperature range from 45 to 85° C. Diphenyl carbonate purities of 97.5 to 99.5% are obtained. A disadvantage of this method is the restriction to reaction solutions with a diaryl carbonate content of more than 70 wt %. Reaction solutions with diaryl carbonate contents of less than 70 wt % cannot be processed by this method. They would have to be concentrated to the required contents, e.g. by distillation. During this thermal stress the catalyst system causes side reactions and is deactivated in the process. Therefore this method is uneconomic and cumbersome for reaction solutions with diphenyl carbonate contents of less than 70 wt %.

The object was to find a gentle method for separating and recovering the catalyst systems from diaryl carbonate-containing reaction solutions with different diaryl carbonate contents with high space-time yield, without deactivation of the catalyst system, and under economic, technically realizable and reproducible conditions.

It has now been found that the disadvantages described can be overcome by removing the reaction solution from the reactor, obtaining a catalyst-containing melt in a suspension crystallization, preferably by inoculation of the reaction solution, separating residues of the catalyst system from the crystallizate with a water-free wash solution, preferably a mixture of diaryl carbonate and aromatic hydroxy compound, working up the crystallizates consisting of a mixture of diaryl carbonate and aromatic hydroxy compound into high-purity diaryl carbonate by crystallization or distillation and afterwards returning the reaction solution containing the catalyst system into the reactor. The wash solution can then be fed to the reaction, without further treatment, as feed replenishment of the aromatic hydroxy compound. Surprisingly it was found that in the case of the diaryl carbonate/phenol system the composition of the crystallizates varies as a function of the diaryl carbonate content of the reaction solution. The 1:1 adduct occurred only in a very narrow concentration range. Only such a quantity of diaryl carbonate is separated from the reaction solution by crystallization as is produced afresh by the reaction and is required for the washing of the crystallizates. The residual content in diaryl carbonate is fed to the reactor again together with the other constituents of the mother liquor. Thermal damaging of the catalyst system does not take place, thus reducing catalyst deactivation to a minimum. A particular advantage of the method according to the invention consists in the fact that reaction solutions having diaryl carbonate contents of 20 to 70% can be used. In addition, different diaryl carbonates may be contained in the reaction solutions useable.

Consequently the invention relates to a method for recovering catalyst systems containing a platinum-group-metal catalyst, a co-catalyst, a quaternary salt and a base from reaction solutions for producing diaryl carbonates of the formula $$R-O-CO-O-R \qquad (I)$$

by oxidative carbonylation of the parent aromatic hydroxy compounds of the formula $$R-O-H \qquad (II),$$

wherein in the formulae

R denotes substituted or non-substituted $C_6$–$C_{15}$-aryl, preferably substituted or non-substituted phenyl, particularly preferably non-substituted phenyl, and having a diaryl carbonate content of 20 to 70 wt %, preferably 20 to 50 wt %, referred to the total weight of the reaction solutions, which is characterised in that a) the reaction solution is transferred from the reactor for producing the diaryl carbonate into an apparatus suitable for the suspension crystallization, b) the suspension crystallization is initiated in the suitable apparatus by temperature reduction, c) the crystallizate obtained, consisting predominantly of diaryl carbonate and the parent aromatic hydroxy compound, is separated from the residual catalyst-containing mother liquor, d) the crystallizate is worked up to pure diaryl carbonate and pure aromatic hydroxy compound and e) the catalyst-containing mother liquor is recycled into the reactor for producing diaryl carbonate or worked up in order to obtain valuable materials.

R is $C_6$–$C_{15}$-aryl, such as phenyl, biphenylyl, naphthyl, anthryl or HO—$C_6H_4$—C(CH$_3$)$_2$—$C_6H_4$— (i.e. ROH is bisphenol A), preferably phenyl. The aromatic rings can each be substituted once or twice by —CH$_3$, —C$_2$H$_5$, —Cl, —Br or —F; particularly preferably R is non-substituted phenyl.

To carry out the method according to the invention, crystallization technologies such as are described in detail for example in Chem.-Ing.-Techn. 57 (1985) 91 ff.can be used. The frequently used agitated vessel crystallizers, cf. Chem.-Ing.-Techn. 57 (1985) p.95, can be dimensioned according to instructions and recommendations of Ullmann's Encyclopedia of Industrial Chemistry, Vol. B 2. Unit Operations I (1988), Chapter 25: Stirring. These methods are carried out discontinuously or continuously. All the apparatuses have heat exchange surfaces and a coolant circuit; the temperatures given below are those of the coolant running back from the heat exchange surfaces.

The following descriptions refer by way of example to diphenyl carbonate (DPC). However, the person skilled in the art can easily adapt the process parameters to account for the physical data of other diaryl carbonates.

For example the suspension crystallization can be carried out in a discontinuous agitated vessel crystallizer with an anchor agitator or cross-arm paddle agitator without baffles and at a specific agitation rate P/V of 0.2 to 0.5 W/l. In this case, for example, a cooling rate from the crystallization point up to the final cooling temperature of 1 K/h is set, but cooling rates of 0.01 to 20 K/h are also possible. The initial temperature for the cooling is dependent on the weighed portion concentration, the final cooling temperature on the desired suspension concentration. The inoculation preferably carried out takes place at the crystallization point with DPC or adduct (0.02 to 1% referred to DPC used). A post-agitation time of 1 to 2 hours is preferably observed at the final cooling temperature. The catalyst-containing mother liquor obtained can be separated from the crystallizate by known methods such as decanting off, pressing off, centrifuging etc. The crystallizate is worked up to pure diaryl carbonate and pure aromatic hydroxy compound, for example by distillation, solution crystallization, extraction or other known methods. The mother liquor separated is returned as a catalyst system into the reactor for producing diaryl carbonate together with other mother liquors obtained during the washing or worked up in order to obtain valuable materials, for instance the platinum-group metal. The returning is the more important use. In a preferred manner, the crystallizate is prior to the working up to pure diaryl carbonate and pure aromatic hydroxy compound washed with a water-free wash solution, for example by suspending the crystallizate in the wash solution. This wash solution is preferably one intrinsic to the system, namely a mixture of diaryl carbonate and aromatic hydroxy compound or the aromatic hydroxy compound alone. The wash solution is, in a preferred manner, united with the mother liquor of the crystallization and returned into the production of the diaryl carbonate. In a preferred manner, the wash solution is a 10 to 25 wt.-% solution of diaryl carbonate in the aromatic hydroxy compound. In a further preferred manner the use of the wash solution is carried out in an amount of 50 to 250 wt.-%, relative to the amount of crystallizate, in such a way that portions of the wash solution are used in several operations, for example in such a way that the crystallizate is first of all suspended in 25 to 40 wt. % of the total amount of wash fluid and then filtered and thereafter again suspended in 60 to 75 wt. % of the total amount of wash fluid and then filtered.

The following examples are intended to show clearly the procedure, but without giving cause for limitations. Tetrabutylammonium bromide (TBAB) is regarded as a main contaminant in the examples. TBAB represents a tracer substance which occurs in the highest concentration in the feed and is most easily measurable as a purification factor in the crystallizate. The reaction solutions can be obtained by known methods for producing diaryl carbonates, for example according to DE-A 19 605 167. Only the relevant constituents DPC, phenol and TBAB, however, are mentioned in the following examples.

EXAMPLES

As given in the following tables (in Example 1: 235.9 g DPC, 270.6 g phenol, 5.2 g TBAB; balance: catalyst), reaction solutions containing DPC, phenol and TBAB, were introduced as feed into an agitated vessel crystallizer; a quasi-continuous mode of operation can be achieved by charging several crystallizers in turn. The temperature was 53° C. at the start; the temperature during the inoculation and hence at the start of the crystallization is given in each case. After a holding time the mother liquor was separated by means of a filter. Thereafter the crystallizate was suspended in the specified wash fluid and separated once again; the wash liquor thereby obtained was combined with the mother liquor and used for the production of further reaction solutions (during repeated recycling a portion of a few per cent of the recycle flow is removed and replaced). The crystallizate was worked up by distillation. The following tables give detailed figures.

$$*\text{TBAB depletion factor} = \frac{\text{mass TBAB feed}/\text{mass DPC feed}}{\text{mass TBAB pure melt}/\text{mass DPC pure melt}}$$

Example 1: 46.0% DPC

| crystallization conditions | | |
| --- | --- | --- |
| crystallization temperature | [° C.] | 46 |
| inoculation temperature | [° C.] | 46 |
| final cooling temperature | [° C.] | 43 |
| cooling rate | [K/h] | 1 |
| cooling time | [h] | 3 |
| holding time | [h] | 2 |

| | mass [g] | DPC [g] | Phenol [g] | TBAB [g] | Depletion factor TBAB |
| --- | --- | --- | --- | --- | --- |
| feed | 512.9 | 235.9 | 270.6 | 5.2 | |
| wash fluid | 300.0 | 60.0 | 240.0 | — | |
| motherliquor | 248.9 | 88.0 | 157.0 | 3.9 | |
| wash liquor | 414.0 | 115.9 | 295.6 | 1.3 | |
| crystallizate | 150.0 | 92.0 | 58.0 | 0.03 | 70 |

| space-time yield | [kg/m$^3$*h] | 36.1 |
| --- | --- | --- |
| DPC yield | [%] | 39.0 |

Example 2: 44.3% DPC

| crystallization conditions | | |
| --- | --- | --- |
| crystallization temperature | [° C.] | 45 |
| inoculation temperature | [° C.] | 45 |
| final cooling temperature | [° C.] | 43 |
| cooling rate | [K/h] | 1 |
| cooling time | [h] | 2 |
| holding time | [h] | 2 |

-continued

|  | mass [g] | DPC [g] | Phenol [g] | TBAB [g] | Depletion factor TBAB |
|---|---|---|---|---|---|
| feed | 570.3 | 252.4 | 310.2 | 6.3 | |
| wash fluid | 200.0 | 40.0 | 160.0 | — | |
| mother liquor | 321.1 | 113.2 | 203.0 | 4.9 | |
| wash liquor | 278.2 | 77.2 | 198.2 | 1.3 | |
| crystillizate | 171.0 | 102.0 | 69.0 | 0.05 | 47 |

|  |  |  |
|---|---|---|
| space-time yield | [kg/m³*h] | 44.7 |
| DPC yield | [%] | 40.5 |

Example 3: 46.9% DPC, filtering without washing

| crystallization conditions | | |
|---|---|---|
| crystallization temperature | [° C.] | 46 |
| inoculation temperature | [° C.] | 46 |
| final cooling temperature | [° C.] | 41 |
| cooling rate | [K/h] | 1 |
| cooling time | [h] | 5 |
| holding time | [h] | 2 |

|  | mass [g] | DPC [g] | phenol [g] | TBAB [g] | depletion factor TBAB |
|---|---|---|---|---|---|
| feed | 520.2 | 243.8 | 269.5 | 5.5 | |
| mother liquor | 317.5 | 121.5 | 189.3 | 5.26 | |
| crystallizate | 202.7 | 122.3 | 80.2 | 0.24 | 11.3 |

|  |  |  |
|---|---|---|
| space-time yield | [kg/m³*h] | 34.3 |
| DPC yield | [%] | 50.1 |

We claim:

1. A method for recovering catalyst systems containing a platinum-group-metal catalyst, a co-catalyst, a quaternary salt and a base from a reaction solution for producing diaryl carbonates of the formula $$R-O-CO-O-R \quad (I)$$

by oxidative carbonylation of the parent aromatic hydroxy compounds of the formula $$R-O-H \quad (II),$$

wherein in the formulae

R signifies substituted or non-substituted $C_6-C_{15}$-aryl, and having a diaryl carbonate content of 20 to 70 wt %, relative to the total weight of the reaction solution, wherein a) the reaction solution is transferred from a reactor for producing the diaryl carbonate into an apparatus suitable for suspension crystallization, b) the suspension crystallization is initiated in said suitable apparatus by temperature reduction to form a crystallizate, c) said crystallizate, which consists predominantly of diaryl carbonate and the parent aromatic hydroxy compound, is separated from residual catalyst-containing mother liquor, said separated crystallizate is washed with a water-free wash solution comprising the aromatic hydroxy compound or a mixture of diaryl carbonate and aromatic hydroxy compound, and the wash solution is recycled into the production of diaryl carbonate, d) said crystallizate is worked up to pure diaryl carbonate and pure aromatic hydroxy compound, and e) said catalyst-containing mother liquor is recycled into said reactor for producing diaryl carbonate or is worked up to recover said platinum-group-metal catalyst.

2. The method of claim 1, wherein the temperature of the reaction solution is reduced with a cooling rate of 20 to 0.1 K/h.

3. The method of claim 1, wherein in step b) the initiation of the suspension crystallization is undertaken, apart from by temperature reduction, in addition by inoculation with solid diaryl carbonate, solid aromatic hydroxy compound or a mixture of both as inoculation material.

4. The method of claim 3, wherein 0.02 to 1 wt % of inoculation material, relative to the diaryl carbonate present in the reaction solution, is used.

5. The method of claim 3, wherein crystallizate from a previous reaction run is used for the inoculation.

6. The method of claim 1, wherein the wash solution is a 10 to 25 wt % solution of diaryl carbonate in the aromatic hydroxy compound.

7. The method of claim 6, wherein the wash solution is used in an amount of 50 to 250 wt %, relative to the amount of crystallizate, and the crystallizate is first suspended in 25 to 40 wt % of the total amount of wash fluid and then filtered and thereafter suspended once again in 60 to 75 wt % of the total amount of wash fluid and then filtered.

* * * * *